(12) United States Patent
Sorrentino et al.

(10) Patent No.: US 8,628,264 B2
(45) Date of Patent: Jan. 14, 2014

(54) ORAL CARE IMPLEMENT

(71) Applicant: Colgate-Palmolive Company, New York, NY (US)

(72) Inventors: Alan Sorrentino, Cranbury, NJ (US); Guofeng Xu, Plainsboro, NJ (US); Richard Scott Robinson, Belle Mead, NJ (US); Douglas J. Hohlbein, Hopewell, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/633,409

(22) Filed: Oct. 2, 2012

(65) Prior Publication Data

US 2013/0025081 A1    Jan. 31, 2013

Related U.S. Application Data

(63) Continuation of application No. 12/147,087, filed on Jun. 26, 2008, now Pat. No. 8,282,298.

(51) Int. Cl.
*B43K 5/14*    (2006.01)

(52) U.S. Cl.
USPC ................. 401/132; 401/16; 401/37; 401/195

(58) Field of Classification Search
USPC ...................... 401/132, 16, 37, 195
See application file for complete search history.

(56) References Cited

U.S. PATENT DOCUMENTS

| | | |
|---|---|---|
| 792,471 A | 6/1905 | Smith |
| 846,900 A | 3/1907 | Bloom |
| 876,185 A | 1/1908 | Hillman |
| 1,214,556 A | 2/1917 | Vene et al. |
| 1,256,662 A | 2/1918 | Cleman et al. |

(Continued)

FOREIGN PATENT DOCUMENTS

| | | |
|---|---|---|
| CA | 2236416 | 5/1997 |
| CH | 664271 | 2/1988 |

(Continued)

OTHER PUBLICATIONS

International Search Report, related to corresponding Internal Application No. PCT/US2006/016510, mailed Nov. 22, 2005.

(Continued)

*Primary Examiner* — David Walczak
*Assistant Examiner* — Bradley Oliver
(74) *Attorney, Agent, or Firm* — Ryan M. Flandro

(57) ABSTRACT

An oral care implement includes a handle, a head mounted to one end of the handle that includes a first face having a plurality of tooth cleaning elements extending therefrom and a second face, a store of dentifrice retained at the head, and a film matrix retained at the head containing at least one rapidly releasable agent. A soft tissue cleaner can be included on the second face. The at least one rapidly releasable agent can be provided to the first and/or second faces during use from the film matrix. In addition, dentifrice can be provided to the first and/or second faces during use from the store of dentifrice. The at least one rapidly releasable agent can include, for example, a flavoring agent, a dentifrice, or a therapeutic agent. The toothbrush can be small in size and lightweight so as to be readily portable for use away from the home.

8 Claims, 9 Drawing Sheets

(56) References Cited

U.S. PATENT DOCUMENTS

| | | |
|---|---|---|
| 1,411,681 A | 4/1922 | Burlew |
| 1,500,722 A | 7/1924 | Roush |
| 1,602,531 A | 10/1926 | Itoh |
| 1,784,986 A | 12/1930 | Eisenberg |
| 1,796,367 A | 3/1931 | Grove |
| 1,797,946 A | 3/1931 | Emil |
| 1,944,067 A | 6/1931 | Simon |
| RE19,006 E | 11/1933 | Graves |
| 1,950,767 A | 3/1934 | Abbott |
| 1,968,303 A | 7/1934 | McMath |
| D94,503 S | 2/1935 | Hadley |
| 1,995,374 A | 3/1935 | Young |
| 2,077,758 A | 4/1937 | Johnson et al. |
| D112,719 S | 12/1938 | Miller |
| 2,233,831 A | 3/1941 | Burke |
| 2,241,584 A | 5/1941 | Cohen |
| 2,259,928 A | 10/1941 | Eaton |
| 2,262,982 A | 11/1941 | Wolcott |
| 2,307,493 A | 1/1943 | Davidson |
| 2,386,085 A | 10/1945 | Babel |
| D161,873 S | 2/1951 | Rosengard |
| 2,649,959 A | 8/1953 | Hallahan |
| 2,710,982 A | 6/1955 | Gillem |
| 2,736,917 A | 3/1956 | Young |
| 2,778,045 A | 1/1957 | Bly et al. |
| 2,793,381 A | 5/1957 | McWhorter |
| 2,813,290 A | 11/1957 | Aschenbach |
| 3,068,571 A | 12/1962 | Thompson |
| 3,078,856 A | 2/1963 | Bender et al. |
| 3,103,935 A | 9/1963 | Woodrow |
| 3,148,684 A | 9/1964 | Keeler |
| 3,165,776 A | 1/1965 | Tuseth |
| 3,301,267 A | 1/1967 | Gerardi et al. |
| 3,316,580 A | 5/1967 | Tebbs |
| 3,432,245 A | 3/1969 | Hudson |
| 3,458,268 A | 7/1969 | Wozab et al. |
| 3,491,396 A | 1/1970 | Granieri, Jr. et al. |
| 3,501,243 A | 3/1970 | Heiskell et al. |
| 3,536,410 A | 10/1970 | Wargoe |
| 3,589,823 A | 6/1971 | Hendrickson |
| 3,609,789 A | 10/1971 | Slater |
| 3,698,405 A | 10/1972 | Walker |
| 3,879,139 A | 4/1975 | Dahl et al. |
| 3,917,420 A | 11/1975 | Watson |
| 1,575,317 A | 3/1976 | Carmichael |
| 4,039,261 A | 8/1977 | Evans |
| 4,194,290 A | 3/1980 | Vallhonrat |
| 4,292,304 A | 9/1981 | Barels et al. |
| 4,427,116 A | 1/1984 | Brown |
| D278,863 S | 5/1985 | Bradley |
| 4,598,437 A | 7/1986 | Ernest et al. |
| 4,610,045 A | 9/1986 | Rauch |
| 4,628,564 A | 12/1986 | Youssef |
| 4,690,816 A | 9/1987 | Hata et al. |
| 4,829,621 A | 5/1989 | Phenegar |
| 4,864,676 A | 9/1989 | Schaiper |
| 4,911,187 A | 3/1990 | Castillo |
| 4,961,717 A | 10/1990 | Hickey |
| 5,045,305 A | 9/1991 | Clarkson |
| 5,052,071 A | 10/1991 | Halm |
| 5,061,106 A | 10/1991 | Kent |
| 5,133,971 A | 7/1992 | Copelan et al. |
| 5,145,668 A | 9/1992 | Chow |
| 5,184,719 A | 2/1993 | Gordon |
| 5,213,428 A | 5/1993 | Salman |
| 5,309,590 A | 5/1994 | Giuliani et al. |
| 5,366,310 A | 11/1994 | Armelles Flors |
| 5,390,984 A | 2/1995 | Boucherie et al. |
| 5,393,796 A | 2/1995 | Halberstadt et al. |
| 5,398,367 A | 3/1995 | Lu |
| 5,476,333 A | 12/1995 | Matthews |
| 5,490,530 A | 2/1996 | Snowden |
| 5,522,109 A | 6/1996 | Chan |
| 5,533,791 A | 7/1996 | Boucherie et al. |
| D378,166 S | 2/1997 | Savitt et al. |
| 5,609,890 A | 3/1997 | Boucherie et al. |
| D378,711 S | 4/1997 | Occhetti |
| 5,633,083 A | 5/1997 | Iwai et al. |
| 5,860,183 A | 1/1999 | Kam |
| 5,888,002 A | 3/1999 | Fernstersheib |
| 5,915,868 A | 6/1999 | Frazell |
| 6,004,059 A | 12/1999 | Zaccaria |
| 6,007,795 A * | 12/1999 | Masterman et al. ............ 424/49 |
| 6,018,840 A | 2/2000 | Guay et al. |
| 6,090,488 A | 7/2000 | Kweon |
| 6,096,328 A | 8/2000 | Sagel et al. |
| 6,135,274 A | 10/2000 | James |
| D435,347 S | 12/2000 | Rumsey, Jr. |
| 6,158,444 A | 12/2000 | Weihrauch |
| 6,179,503 B1 | 1/2001 | Taghavi-Khanghah |
| 6,321,407 B1 | 11/2001 | Weihrauch |
| 6,397,860 B1 | 6/2002 | Hill |
| 6,401,291 B1 | 6/2002 | Lee |
| 6,463,618 B1 | 10/2002 | Zimmer |
| 6,514,483 B2 | 2/2003 | Xu et al. |
| 6,524,023 B2 | 2/2003 | Andersen |
| 6,526,993 B1 | 3/2003 | Wagner |
| 6,602,013 B2 | 8/2003 | Clark |
| 6,669,929 B1 | 12/2003 | Boyd et al. |
| D487,351 S | 3/2004 | Frazell |
| 7,039,984 B1 | 5/2006 | Watanabe et al. |
| D527,528 S | 9/2006 | Hohlbein |
| D528,803 S | 9/2006 | Hohlbein |
| D532,202 S | 11/2006 | Hohlbein |
| D532,607 S | 11/2006 | Hohlbein |
| 7,478,959 B2 | 1/2009 | Hohlbein |
| 2002/0106234 A1 | 8/2002 | Johnson |
| 2002/0152538 A1 | 10/2002 | McDevitt et al. |
| 2002/0175101 A1 * | 11/2002 | Albert ........................ 206/362.2 |
| 2003/0039504 A1 | 2/2003 | Clark |
| 2003/0100908 A1 | 5/2003 | Grumberg et al. |
| 2003/0188761 A1 | 10/2003 | Garcia et al. |
| 2004/0136924 A1 | 7/2004 | Boff et al. |
| 2004/0237226 A1 | 12/2004 | Hohlbein et al. |
| 2005/0069372 A1 | 3/2005 | Hohlbein et al. |
| 2005/0106112 A1 | 5/2005 | Boyd et al. |
| 2006/0165473 A1 | 7/2006 | Hohlbein |
| 2008/0014010 A1 * | 1/2008 | Bartschi et al. ............... 401/146 |
| 2008/0104786 A1 | 5/2008 | Hohlbein et al. |
| 2008/0120798 A1 | 5/2008 | Sorrentino et al. |
| 2009/0044356 A1 | 2/2009 | Noble et al. |
| 2009/0208568 A1 | 8/2009 | Hannetel et al. |
| 2009/0320226 A1 | 12/2009 | Robinson et al. |

FOREIGN PATENT DOCUMENTS

| | | |
|---|---|---|
| CN | 2111027 | 7/1992 |
| CN | 2420901 | 2/2001 |
| CN | 2469777 | 1/2002 |
| CN | 1694636 | 11/2005 |
| DE | 594479 | 3/1934 |
| DE | 850981 | 9/1952 |
| DE | 3529953 | 3/1987 |
| DE | 3638696 | 5/1988 |
| DE | 4127429 | 2/1993 |
| DE | 4231817 | 3/1994 |
| DE | 4238421 | 5/1994 |
| DE | 19531368 | 2/1997 |
| DE | 19842984 | 8/2000 |
| DE | 19925568 | 12/2000 |
| EP | 0332026 | 9/1989 |
| EP | 0475314 | 3/1992 |
| EP | 0481926 | 4/1992 |
| EP | 0872195 | 10/1998 |
| EP | 1415572 | 5/2004 |
| EP | 1639913 | 3/2006 |
| ES | 2090287 | 10/1996 |
| FR | 2550429 | 2/1985 |
| FR | 2554331 | 5/1985 |
| FR | 2602129 | 2/1988 |
| FR | 2646068 | 10/1990 |
| FR | 2654598 | 5/1991 |
| FR | 2754436 | 4/1998 |
| FR | 2772569 | 6/1999 |

(56) References Cited

FOREIGN PATENT DOCUMENTS

| | | |
|---|---|---|
| FR | 2772571 | 6/1999 |
| FR | 2822658 | 10/2002 |
| FR | 2832632 | 5/2003 |
| GB | 228460 | 2/1925 |
| GB | 746649 | 3/1956 |
| GB | 2297489 | 8/1996 |
| GB | 2351015 | 12/2000 |
| GB | 2388529 | 11/2003 |
| GB | 2394653 | 5/2004 |
| JP | 5192227 | 8/1993 |
| JP | 3043427 | 11/1997 |
| JP | 10216158 | 8/1998 |
| JP | 10262732 | 10/1998 |
| JP | 2002142865 | 5/2002 |
| JP | 2003245133 | 9/2003 |
| KR | 102004003756 | 1/2004 |
| SU | 1291019 | 2/1987 |
| SU | 1417859 | 8/1988 |
| TW | 316404 | 9/1997 |
| WO | WO 87/00425 | 1/1987 |
| WO | WO 8700425 | 1/1987 |
| WO | WO 97/16995 | 5/1997 |
| WO | WO 98/57570 | 12/1998 |
| WO | WO 9923910 | 5/1999 |
| WO | WO 99/60886 | 12/1999 |
| WO | WO 01/26504 | 4/2001 |
| WO | WO 02/15736 | 2/2002 |
| WO | WO 02/26079 | 4/2002 |
| WO | WO 02/34083 | 5/2002 |
| WO | WO 02/058508 | 8/2002 |
| WO | WO 03/037210 | 5/2003 |
| WO | WO 2004/021914 | 3/2004 |
| WO | WO 2004/010821 | 5/2004 |
| WO | WO 2004/087089 | 10/2004 |
| WO | WO 2005/110149 | 11/2005 |
| WO | WO2006/020700 * | 2/2006 |
| WO | WO 2007149919 | 12/2007 |
| WO | WO 2008/103597 | 8/2008 |
| WO | WO 2009/136911 | 11/2009 |

OTHER PUBLICATIONS

International Search Report, related to corresponding Internal Application No. PCT/US2006/062416, mailed Apr. 18, 2007.
International Search Report, related to corresponding Internal Application No. PCT/US2009/030090, mailed Apr. 3, 2009.
International Search Report and Written Opinion in International Application No. PCT/US2011/0030720 mailed Jul. 6, 2011.
National Research Council (U.S.) Food Protection Committee, 1965, *Chemicals Used in Food Processing*, Washington, Publication No. 1274, pp. 63-258.

* cited by examiner

ORAL CARE IMPLEMENT

CROSS-REFERENCE TO RELATED APPLICATIONS

The present application is a continuation of U.S. patent application Ser. No. 12/147,087, filed on Jun. 26, 2008, the entirety of which is hereby incorporated by reference.

BACKGROUND OF THE INVENTION

The present application relates generally to oral care implements, such as toothbrushes, soft tissue cleaners and combined tooth cleaning/soft tissue cleaning devices, and, more particularly, to an oral care implement having a dispenser, such as a store of releasable dentifrice, and a film matrix containing a rapidly releasable agent.

The advantages of good dental hygiene are well known. Often, however, toothbrushes are forgotten when one is traveling or away from home. Hotels, health care facilities, nursing homes, hospitals, daycare facilities, schools, airlines, etc. have a need for single use disposable or limited multiple use toothbrushes that can be economically supplied to and discarded by individuals without a toothbrush and/or a water supply. Such toothbrushes could be used in vending machines, or distributed in large quantities for simple, portable use from anywhere.

Various types of disposable, limited use, or portable toothbrushes are known in the art. For example, some toothbrush systems have attempted to meet some of these needs by providing toothpaste within the toothbrush itself, through an integrated channel, for distribution through the toothbrush and around the bristles. This approach can be less economical due to the added manufacturing costs of toothbrushes with integrated channels. In addition, the toothpaste in some of these integrated channel toothbrushes, not being properly sealed, has a tendency to become dry, hard and stale. Further, these types of toothbrushes attempt to provide basic teeth cleaning without effectively engaging soft oral tissues or providing effective tongue cleaning.

BRIEF SUMMARY OF THE INVENTION

The various features described herein can help improve dental care by providing enhanced dispensing of a dentifrice along with superior cleaning of teeth and/or soft oral tissues.

In one embodiment, the invention can be an oral care implement comprising: a handle; a head having a first face and a second face; tooth cleaning elements extending from the first face of the head and soft tissue cleaning elements extending from the second face of the head; a store of dentifrice retained at the head; a film matrix containing at least one rapidly releasable agent, the film matrix comprising a plurality of discrete film matrix particles; and wherein the film matrix particles are attached to the soft tissue cleaning elements.

In another embodiment, the invention can be an oral care implement comprising: a handle; a head having a first face and a second face, a recess formed into the head at the second face; tooth cleaning elements extending from the first face of the head and soft tissue cleaning elements extending from the second face of the head; a store of dentifrice retained at the head; and a film matrix containing at least one rapidly releasable agent, wherein the film matrix comprises a film strip disposed within the recess.

In yet another embodiment, the invention can be an oral care implement comprising: a handle; a head; an arrangement of tooth cleaning elements on a first surface of the head; a first path providing a first flow of dentifrice from a store of dentifrice retained at the head to the tooth cleaning elements; an arrangement of soft tissue cleaning elements on a second surface of the head; a film matrix containing at least one rapidly releasable agent disposed within a recess formed into the second surface of the head, the at least one rapidly releasable agent flowing to the soft tissue cleaning elements during use of the oral care implement; and wherein upon depletion of the film matrix from the recess, the recess forms a second path providing a second flow of dentifrice from the store of dentifrice to the soft tissue cleaning elements.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features herein will become more fully understood from the detailed description given herein below, and the accompanying drawings, which are given by way of non-limiting illustration only.

DETAILED DESCRIPTION OF THE INVENTION

Figure 1:
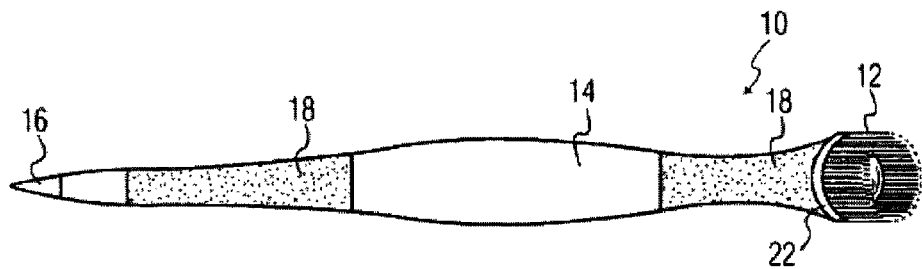
FIG. 1 is a front view of an oral care toothbrush with a toothpick and a store of dentifrice connected thereto.

The following detailed description refers to the accompanying drawings. The same reference numbers in different figures identify the same or similar elements.

FIGS. 1-4 illustrate an oral care toothbrush 10 that includes a head 12 and a handle 14. Head 12 can be a refill head and thus can be removably connected to handle 14, or head 12 can be permanently connected to handle 14.

The majority of handle 14 and a portion of head 12 can be molded from a variety of rigid materials, including plastics, resins, etc., such as, for example, polypropylene. An end portion of handle 14, is attached to an accessory, preferably a toothpick 16 formed of a resilient and soft thermoplastic elastomer. Toothpick 16 can be a refill and thus be removably connected to handle 14, or toothpick 16 can be permanently connected to handle 14. Toothpick 16 provides a mechanism for spot cleaning between teeth. Forming toothpick 16 of a soft elastomer provides more comfortable interproximal cleaning between teeth. Toothpick 16 could, however, be made of a stiff rigid material similar to the main portion of handle 14, or could simply be a rubber or elastomeric pick adhered or otherwise mounted to the end of handle 14.

Portions 18 of handle 14 can also be formed of a resilient and soft thermoplastic elastomer. The thermoplastic elastomer which forms toothpick 16 and handle portions 18 can be a thermoplastic vulcanate (TPV) consisting of a mixture of polypropylene and EPDM (ethylene propylene diene monomers) which is available as SANTOPRENE (brand), described in U.S. Pat. No. 5,393,796, or VYRAM (brand), another TPV consisting of a mixture of polypropylene and natural rubber. Both SANTOPRENE and VYRAM (brands) are elastomers marketed by Advanced Elastomer Systems. Other suitable elastomers include KRATON, a brand of styrene block copolymer (SBC) marketed by Shell, and DYNAFLEX G 2706 (brand), a thermoplastic elastomer marketed by GLS Corporation and which is made with KRATON (brand) polymer.

Handle 14 can further include dimples, bumps, or ridges protruding from portions of its surface, and providing a decorative appearance to handle 14 and enhanced gripping of handle 14 during use of toothbrush 10. The dimples can be formed from the same material as soft elastomer portions 18 of handle 14 or from the same material as the majority of handle 14 (e.g., a rigid material such as polypropylene). All or part of handle 14 could be made of any suitable material, such as plastic, wood, metal or various natural materials which are biodegradable. Preferably handle 14 is made of a generally flat or oval shape rather than cylindrical in its gripping portion which would be between the spaced elastomer portions 18 to facilitate the gripping of the handle.

Figure 4:
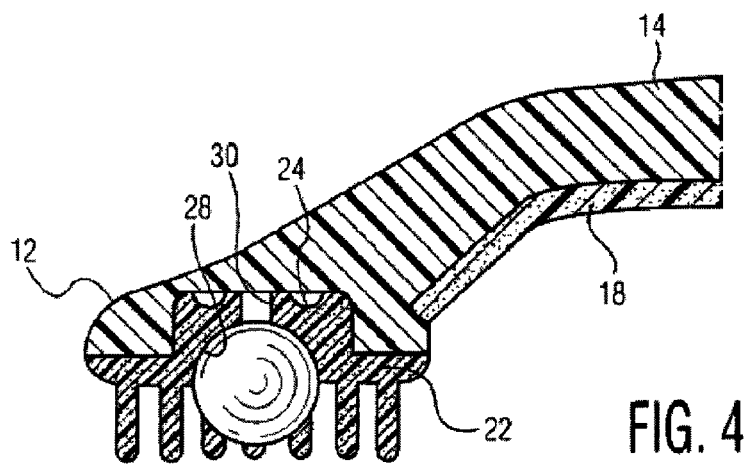
FIG. 4 is a fragmental, cross-sectional view of the head of the toothbrush of FIGS. 1-3.

As shown in FIG. 4 another portion of head 12, defining a bristle or cleaning element block 22 of head 12, can also be formed of a resilient and soft thermoplastic elastomer, such as the thermoplastic elastomer used to form handle portions 18. Cleaning block 22 can include one or more depressions 28 provided in a surface 24 thereof with an opening 30 therein that provides a cushioning effect to a dispenser or store of dentifrice 32, which is illustrated as gel capsule 32, contained therein, as described more fully below. Cleaning element block 22 further includes a multitude of cleaning elements which could be conventional filament, preferably nylon, or elastomeric bristles or fingers 26 extending integrally outwardly from the outer surface of head 12. In the illustrated configuration as best shown in FIG. 4, all of the cleaning elements 26 extend outwardly from the outer surface of cleaning element block 22 the same distance so as to create a generally flat surface. Alternatively, however, some elements 26 can be shorter or longer than other elements 26. The variable length of the cleaning elements 26 is illustrated by the tips 26a shown in dotted lines in FIG. 5, with only body portions 26b of the cleaning elements 26 shown in solid lines for purposes of clarity and to focus on the variable nature of such elements.

The term "cleaning elements" is used herein in a generic sense to refer to cleaning elements or massage elements arranged in a circular cross-section shape or any type of desired shape, including straight portions or sinusoidal portions. It is to be understood that the specific illustration of the cleaning elements is merely for exemplary purposes. The features herein can, however, be practiced with various combinations of the same or different configurations (such as stapled, in-mold tufting (IMT) bristle technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while FIGS. 1-4 illustrate the cleaning elements 26 to be generally perpendicular to the outer surface of head 12, some or all of the cleaning elements 26 can be positioned at various angles with respect to the outer surface of head 12. It is thereby possible to select the combination of configurations, materials and orientations to achieve specific intended results, such as enhanced cleaning, tooth polishing, breath freshening, tooth whitening and/or massaging of the gums.

As stated above, the cleaning block 22 can include one or more depressions 28, which are designed to receive and retain an oral care dispenser, such as a store of dentifrice in the form of rupturable gel capsule 32 therein. The one or more depressions 28 can be varied in size so as to accommodate not only varying size dispensers 32, but also varying quantities of toothpowder, toothpaste, tooth cleaning gel dentifrice or other oral care material. While the present invention can be manufactured containing a packed toothpowder, toothpaste or tooth cleaning gel dentifrice and used repeatedly by the user refilling the dispenser with toothpowder, toothpaste or tooth cleaning gel dentifrice, it is preferably used with one or more gel capsules 32 contained therein. Most preferably the present invention is used with a single gel capsule 32, supplied therewith, so as to be most easily transported, used, and subsequently disposed of however, it can also be used repeatedly with replaceable gel capsules 32, and then disposed of.

It is preferred that the depression is in the form of a cushioned socket 28 sized and shaped to receive and retain the gel capsule 32, without premature rupture of the gel capsule 32 prior to use thereof during application of the bristle block 22 to the denture and brushing thereof. Cushioning socket 28, opening 30, and the material making up bristle block 22 provide a cushioning effect for gel capsule 32 to prevent gel capsule 32 from rupturing prior to use.

Gel capsule 32 holds and applies a mouth care solution onto bristles 26 of toothbrush head 12. The mouth care solution can be a toothpaste, a gel, a mouthwash, or similar dentifrice or oral hygiene product, or a combination of the same contained in the rupturable capsule 32. Preferably gel capsule 32 is a liquid-filled gel capsule having frangible, thin walls that easily rupture or burst when rubbed against the teeth, or dissolve when mixed with the saliva of a user. The materials making up gel capsule 32 and the oral or mouth care solution contained therein preferably are consumable by the user of toothbrush 10, eliminating the need for water, a sink, or a waste receptacle to expectorate the gel capsule 32 or its contents. The mouth care solution remains in gel capsule 32 until toothbrush 10 is ready for use. Gel capsule 32 can be fully sealed, helping the mouth care solution to remain fresh until use.

The store of dentifrice in the form of a capsule or dispenser 32 can include an active agent. Non-limiting examples of active agents which can be used include antibacterial agents, whitening agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The active agent can be compatible with toothpaste, or can be unstable and/or reactive with typical toothpaste ingredients. The active agent also can be a tooth cleaning agent to boost the overall efficacy of brushing.

The active agent can be provided in any suitable vehicle, such as in aqueous solution or in the form of gel or paste. The vehicle can have a variety of different visual aesthetics including clear solution or gel or opaque solution or gel. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B. F. Goodrich, and combinations thereof. The selection of a suitable vehicle will be apparent to persons skilled in the art depending on such factors as the properties of the active agent and the desired properties of the medium, such as viscosity.

In use, gel capsule 32 would be pressed against the teeth and burst or rupture or dissolve, applying the mouth care solution over cleaning elements 26. The user then can brush his/her teeth with toothbrush 10. The user can also use toothpick 16 to clean between teeth, either before or after brushing. After the user has used toothbrush 10, he/she can, but not necessarily, then easily and economically dispose of toothbrush 10.

In some configurations, the entire structure of toothbrush 10, including head 12, handle 14, and toothpick 16, can be molded as one integral structure, using a conventional two-component injection molding operation typically used in the manufacture of toothbrushes. This enables toothbrush 10 to be economically and quickly manufactured. Although toothbrush 10 can have a variety of sizes and dimensions, it is preferred that toothbrush 10 have a small profile, with head 12 being small enough to cover one tooth at a time and handle 14 being thinner than conventional, everyday toothbrush handles. Toothbrush 10 is thus readily portable or space saving.

The toothbrush 10 can provide many benefits, including the cosmetic benefits of brushing one's teeth in a form that can be used when one is away from home, and away from a water supply. The cosmetic benefits achieved by the toothbrush 10 include the cleaning of debris between teeth with toothpick 16, broad tooth surface cleaning (particularly the front teeth) with cleaning elements 26 and the mouth care solution of gel capsule 32, and breath freshening with the mouth care solution of gel capsule 32.

In addition to the cosmetic benefits, the toothbrush 10 can also provide economic benefits in the form of an inexpensive toothbrush that is both quickly and economically manufactured. Toothbrush 10 also provides a mechanism for maintaining oral health, without the need for toothpaste, water, mouth wash, and containers to hold the same. Thus, toothbrush 10 is also very convenient to use.

Furthermore, the toothbrush 10 provides at least one benefit of preventing the spread of waterborne diseases. For example, the toothbrush 10 eliminates the conventional practice of using local water to mix with toothpaste. This feature is useful for military applications where there is a limited source of potable water or a need to conserve water or maintain the oral health of troops, such as in desert fighting environments. In another situation, the toothbrush is useful in outdoor camping environments to prevent disease or sickness from waterborne bacteria.

Although FIGS. 1-4 illustrate a manually-operated, disposable toothbrush, the features herein can also be practiced where the head includes one or more power or electrically operated movable sections carrying cleaning elements. Such movable section can oscillate in a rotational manner or can oscillate linearly in a longitudinal direction with respect to the longitudinal axis of the head or can oscillate linearly in a lateral or transverse direction with respect to the longitudinal axis of the head. The movable section can oscillate in and out in a direction toward and away from the outer surface of the head. The movable section can rock back and forth with respect to the outer surface of the head. The movable section can rotate continuously in the same direction, rather than oscillate. Any suitable drive mechanism can be used for imparting the desired motion to the movable section. Where plural movable sections are used, all of the movable sections can have the same type and direction of movement, or combinations of different movements can be used.

In some configurations, the cleaning elements can be in the form of bristles made from conventional materials, such as nylon, as well as from a combination of materials so as to provide the proper stiffness in an economical manner. For example, the cleaning elements could be made of a flexible resilient material, such as TPE and a lesser expensive material such as LLDPE (linear low density polyethylene) or EVA (ethylene vinyl acetate) or a TPE. The cleaning elements could be made of a blend of TPE and either LLDPE, EVA, or polypropylene. Preferably, the two materials are combined to provide a stiffness of less than 600 MPa. The blend of materials would give the properties of conventional nylon bristles, while offering reduced costs. For example, there would be lower manufacturing costs by injection molding instead of conventional bristle tufting. Alternatively the resilient material could be a single material, such as hard TPE (i.e. Shore A 80 hardness), straight LLDPE or straight EVA.

The cleaning elements can be of any desired shape. For example, the cleaning elements could be of cylindrical shape having a uniform diameter throughout their length. Alternatively, the cleaning elements could taper from the root of each cleaning element where it extends from head 12 to its outer cleaning end. Since a preferred practice of the invention is to provide a small lightweight toothbrush the dimensions of the various components of toothbrush 10 are preferably small. Thus, for example, each cleaning element can extend outwardly from the outer surface of cleaning element block 22 a distance no greater than 10 mm and preferably no greater than 8 mm and most preferably no greater than 6 mm. Where tapered cleaning elements are used the root diameter should be no greater than 1.5 mm, preferably no greater than 1 mm, most preferably no greater than 0.7 mm or no greater than 0.5 mm or no greater than 0.3 mm. The diameter could then decrease in size to no greater than 0.2 mm at a distance of no greater than 6 mm from the base of the cleaning element. The taper relationship of diameter at a distance location above the root diameter could be a range of no greater than 1 mm at a distance of no greater than 10 mm, preferably no greater than 0.6 mm at a distance of no greater than 8 mm, most preferably no greater than 0.2 mm at a distance of no greater than 6 mm. Preferably, the length of the entire toothbrush 10 is no greater than 5 inches, preferably no greater than 4 inches, and more preferably no greater than 3.75 or 3 or 2.50 inches, and can be in the range of 2 to 4 inches.

Figure 5:
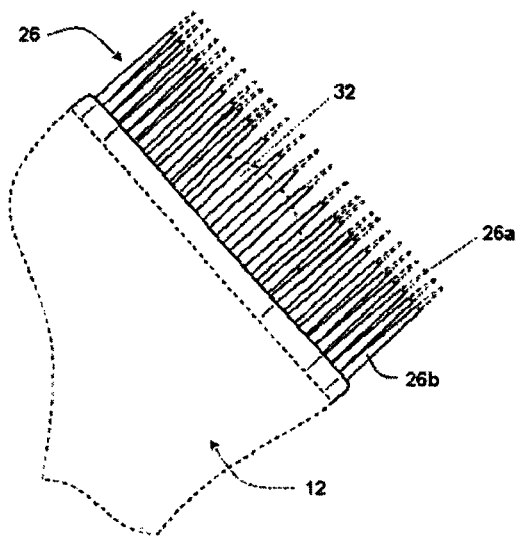
FIG. 5 is a side view of a head of a toothbrush configuration with only portions of the cleaning elements shown in solid lines for purposes of focus and clarity.

As illustrated in FIGS. 1 and 4 the cleaning elements define a cleaning field in the head and the dispenser 32 is mounted within this cleaning field. The cleaning elements 26 preferably extend outwardly from the cleaning block 22 to be approximately flush with the outer surface of the gel bead or capsule 32, as shown in FIG. 4. The features herein, however, can also be practiced where the cleaning elements extend either a greater distance or a lesser distance than the dispenser 32 as shown in FIG. 5. Since toothbrush 10 is intended to be both small and lightweight, it is preferred that toothbrush 10 weigh no more than 3 grams. The small size is such that it can be held completely within the palm of an adult user. Head 12 is of a size that it would correspond to the size of an individual tooth or an individual tooth and the interproximal areas. Head 12 could be made of any suitable shape and is preferably of circular or oval shape having a maximum lateral dimension or diameter of no greater than 13 mm, preferably no greater than 12 mm and most preferably no greater than 11 mm. Where head 12 is of non-circular shape its maximum lateral dimension is 14 mm.

Figure 2:
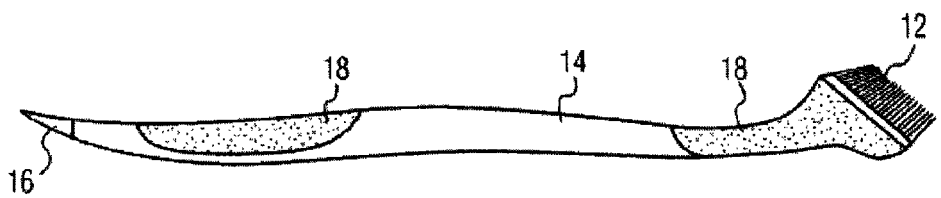
FIG. 2 is a side view of the toothbrush shown in FIG. 1.
Figure 3:
FIG. 3 is a rear view of the toothbrush shown in FIGS. 1-2.

As shown in FIG. 2 head 12 can be at an angle between 0.degree. and 90.degree. to the longitudinal axis of handle 14. The preferred angle is from 20.degree. to 70.degree. and more preferably from 30.degree. to 60.degree. The cleaning elements could be perpendicular to the outer surface of head 12 or could also be at an angle to the outer surface such as in the range of 60.degree. to 90.degree. or in the range of 75.degree. to 90.degree.

In one configuration, the cleaning elements could be hollow, such as hollow bristles, which are capable of absorbing a medicament by capillary action. Such a feature would be particularly useful for children where a medicament or some form of flavor could be dispensed from the hollow cleaning elements. It is also possible to leach antibacterial material from the cleaning elements. In one configuration where the cleaning elements are used to dispense oral care materials the cleaning elements themselves can be considered as the oral care dispensers without requiring additional dispensers such as capsule 32.

Where specific parameters and characteristics have been given for cleaning elements, the features herein could be practiced where other cleaning elements do not include those parameters and characteristics.

Figure 6:
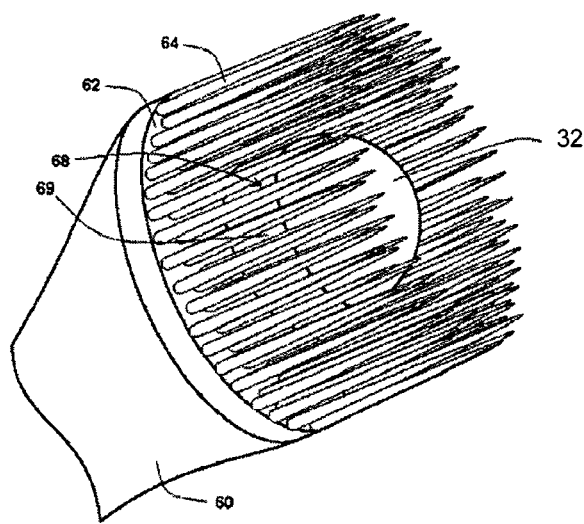
FIG. 6 is a perspective view of one configuration of a toothbrush head.
Figure 7:
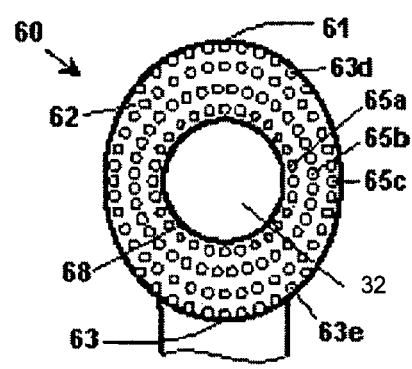
FIG. 7 is an enlarged front view of the head of FIG. 6.

FIGS. 6 and 7 illustrate a head 60 according to another configuration, the head 60 having an outer surface 62, a plurality of cleaning elements 64 extending from a portion of the outer surface 62, and a raised socket 68 extending from another portion of the outer surface 62. The socket 68 can be formed from the same material as the outer surface 62, and can be integrally formed with the outer surface such as by molding or the like. The socket 68 extends outwardly relative to the outer surface 62 by an upstanding wall 69, and includes a seat to accommodate an oral care dispenser such as a bead or capsule 32 as discussed herein. The raised socket 68 positions the dispenser 32 closer to the edges of the cleaning elements 64 to facilitate contact between the dispenser 32 and the user's teeth and to encourage rupturing of the dispenser 32 early in the brushing process. The socket can also position the dispenser 32 beyond the cleaning elements 64 as discussed above, which would encourage even greater and immediate contact with the user's teeth.

The cleaning elements 64 can comprise a variety of configurations as discussed above, such as a circular configuration as shown in FIG. 1. FIG. 7 illustrates an example of an oval configuration, wherein the cleaning elements 64 are arranged in a plurality of concentric rings 65a, 65b, 65c, surrounding the socket 68. One of such rings is a partial ring comprised of partial ring sections 65d, 65e defined along the upper and lower edges 61, 63 of the outer surface 62 of the head 60, which sections 65d, 65e comprise the equivalent of a so-called power tip that is designed to provide a cleaning edge that extends beyond the majority of the field of cleaning elements for increased efficacy.

Any suitable oral care products could be dispensed from the dispenser. Such products include, but are not limited to the gel capsule 32 as previously described and could contain toothpaste, tooth powder or could be a small vial of mouthwash having a gel, a powder or a liquid. Such a vial could be separately included in a package containing the toothbrush. The materials could be flavored and could be provided in sets of different flavors and/or different characteristics such as medicaments, numbing materials, etc.

Where the dispensers 32 are shown as stores of dentifrice in the form of beads, different beads or capsules could be used with different colors/flavors to enhance consumer appeal. As described the capsule 32 could be an impregnated bead that bursts. Suitable beads include those supplied by Mane Inc.

Any suitable methods can be used for forming toothbrush 10 and its various components. For example, multi-component injection molding could be used to integrally couple various components such as the cleaning elements and the head and/or the handle. This could be done in an automated or multiple step process. The handle could be rotocast blow molded to form a hollow squeeze handle that would be usable in the configuration shown in FIG. 11.

As is apparent the features herein provide an oral care toothbrush that can be small in size and portable and can be conveniently used away from home under circumstances, such as travel, where water is not readily available.

The features herein could be practiced with a combination of various components that do not involve "toothbrush" usage. In that sense these features can be used in any oral care device or the like, rather than strictly being a toothbrush. Where used as a toothbrush or the like, the features herein can have the advantages, because of the size and configuration, to allow discreet hygienic use, such as no fingers in the mouth, adapting it to be readily used in public areas.

Figure 8:
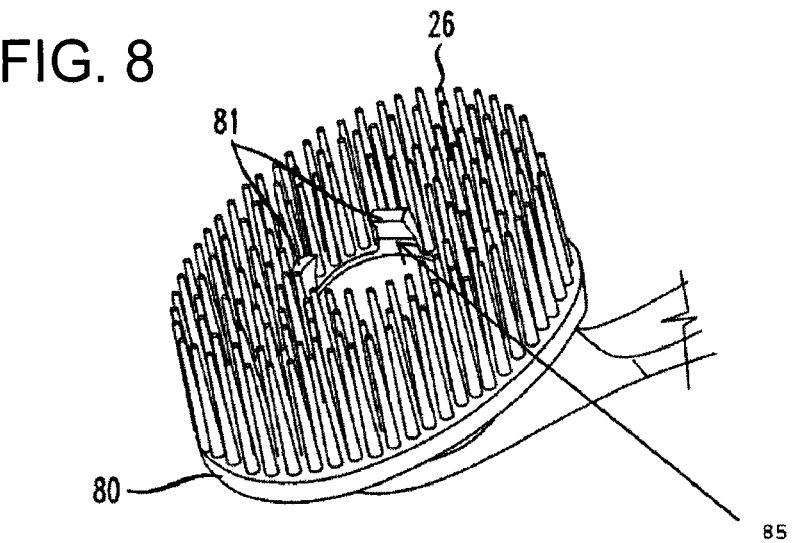
FIG. 8 is a perspective view of an alternate toothbrush head configuration without showing the store of dentifrice.

FIG. 8 illustrates another variation in which the head or carrier 80 can have an oval shape, and which can have a series of retaining members 81, such as prongs or biasing members, to hold an oral care dispenser, such as a store of dentifrice in the form of a bead of packed dentifrice or capsule (not shown in the figure), in place prior to use. The retaining members 81 can help retain the bead or capsule at a higher elevation with respect to the field of oral care elements (e.g., bristles 26), to expose more surface area of the bead, dispenser or capsule 32 to the user's saliva to improve the "mouth-feel" and expedite the dissolving of the bead, dispenser or capsule. As illustrated, the retaining members 81 can retain the bead, dispenser or capsule beneath the distal ends of the bristles 26, so as to keep the bead, dispenser or capsule submerged within the field of bristles 26, such that the bristles extend beyond the bead, dispenser or capsule at the bristles' distal ends.

The retaining members 81 can be made of the same material as the bristles 26, or alternatively they can be made of a different material having greater rigidity than the bristles. In one construction, the retaining members 81 can be made of the same material as elastomer portions 18.

Figure 9:
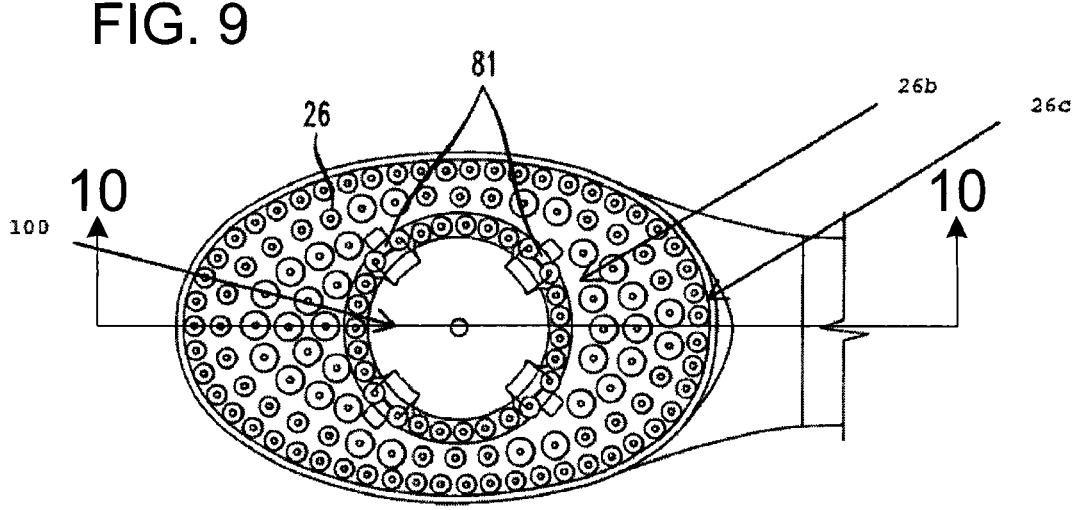
FIG. 9 is an enlarged front view of the head of FIG. 8 without showing the store of dentifrice.

The number of retaining members 81 used can vary depending on the type of bead or capsule, and the amount of retention force assistance. As illustrated in FIG. 9, four retaining members 81 can be used at four cardinal points around the perimeter of the bead or capsule. Greater or fewer retaining members 81 can be used. For example, some configurations might use three retaining members 81 at triangular points around the perimeter, while other configurations might use five, six, or more prongs around the perimeter. The retaining members 81 can be positioned such that the bead or capsule is held in a centered position with respect to the bristles 26.

Figure 17:
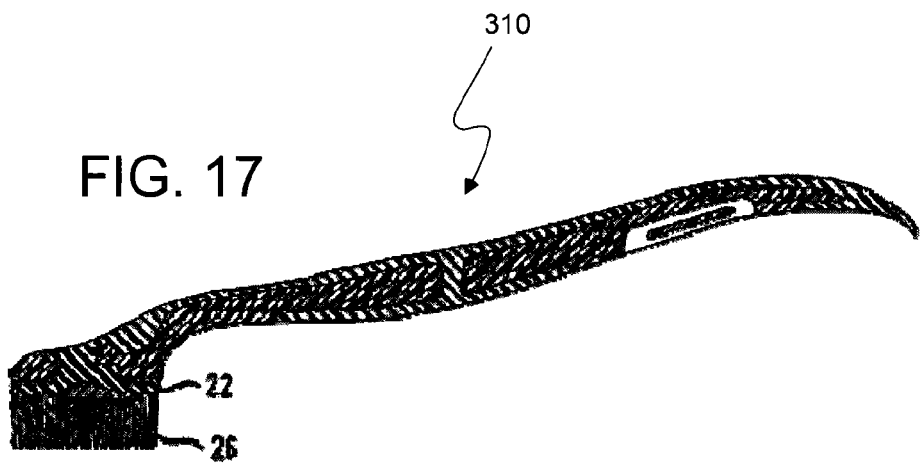
FIG. 17 is a cross-sectional side view of a toothbrush having the head shown in FIG. 11.

As also shown in FIG. 9, the bristles 26 can vary in diameter at their proximate ends, so that bristles in different areas of the field have different thicknesses and rigidity or axial stiffness as measured from the longitudinal axis of the bristle. In such a construction, inner or central region bristles 26b are stiffer than the outer or peripheral region bristles 26c. The bristles 26 of the carrier 80 can taper towards their distal ends, as seen in FIG. 17.

With reference to FIG. 9, the variable stiffness arrangement of the field of bristles 26 forms a structure for incremental radial flow control of oral care solution/material during a brushing operation for efficient cleaning. This feature is particularly useful for low viscosity oral care solutions released from the dispenser 32. Nevertheless, oral care solutions of higher viscosity can be used in the carrier 80. The bristles surrounding retaining members 81 are independently flexible. In this regard, during a brushing operation, the free ends (e.g., tip) of the stiffer bristles 26b bend relative to their, respective vertical axis less than the outer bristles 26c (e.g., bristles near the periphery). Hence, a portion of the dentifrice stays longer in the central region of the brush head by reduced dynamic bending or action of the stiffer bristles. The sweeping or oscillating motion of the carrier 80 transfers a portion of the retained liquid to the outer region of the carrier 80. While the outer bristles 26c are less stiff, the dynamic bending relative to their vertical axis additionally causes the outer bristles to receive a portion of the dentifrice from the central region of the carrier 80. In this construction, effective cleaning of the tissue surfaces in the mouth can be obtained though the combined use of the variable stiffness bristle field mechanically scrubbing the tissue surfaces and the beneficial effects of applying the oral care material from the dispenser in the oral cavity. In this way, the bristles field provides a limited and controlled flow of the dentifrice or other oral care material to the outer bristles and maintains sufficient flexibility to provide greater user comfort and improved cleaning of the oral tissues.

Figure 10:
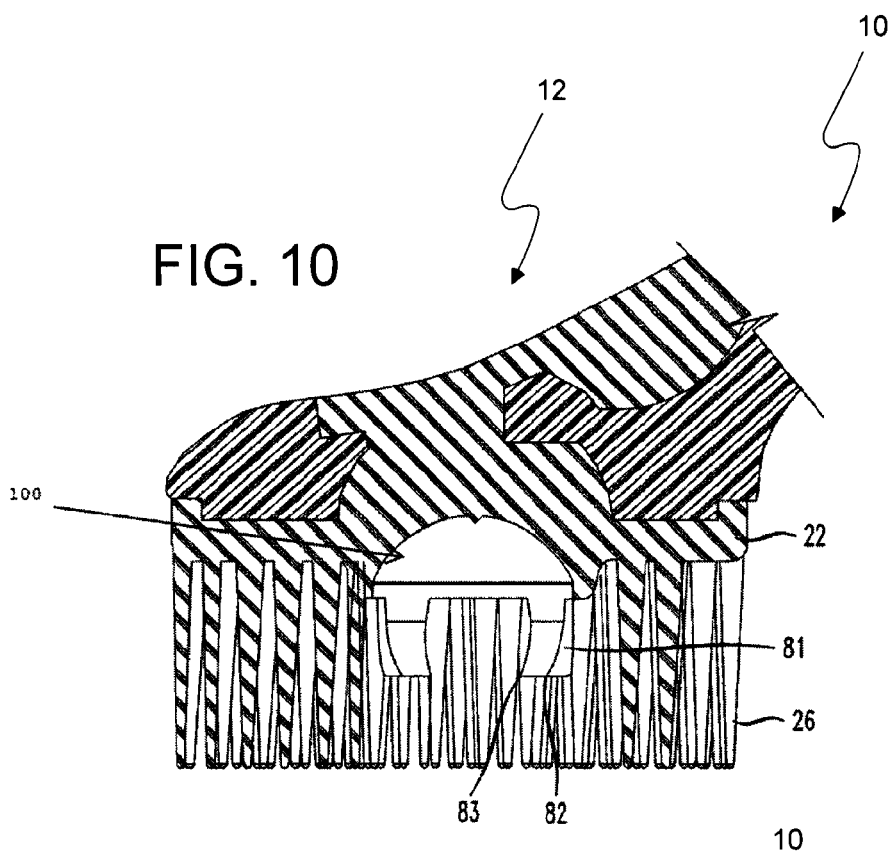
FIG. 10 is an enlarged cross-sectional side view of the head of FIG. 9 without showing the store of dentifrice.

With reference to FIGS. 8-11, in one construction, a basin, or cavity 100 is provided in carrier 80 below the dispenser 32. As can as seen in FIGS. 9 and 10, basin 100 can be a concaved structure or hemispherical structure disposed in the interior area, beneath and between the retaining members 81. While a concaved structure is shown, other shapes for the basin 100 are possible, such as a triangular prism, a square prism or a rectangular prism. The basin 100 serves to retain a portion of the oral care material from the dispenser 32 to extend the beneficial cleaning effects of the oral care material during brushing. In this regard, the sweeping or oscillating motion of the cauier 80 transfers a portion of the retained liquid to inner region bristles 26b of the carrier 80.

Figure 19:
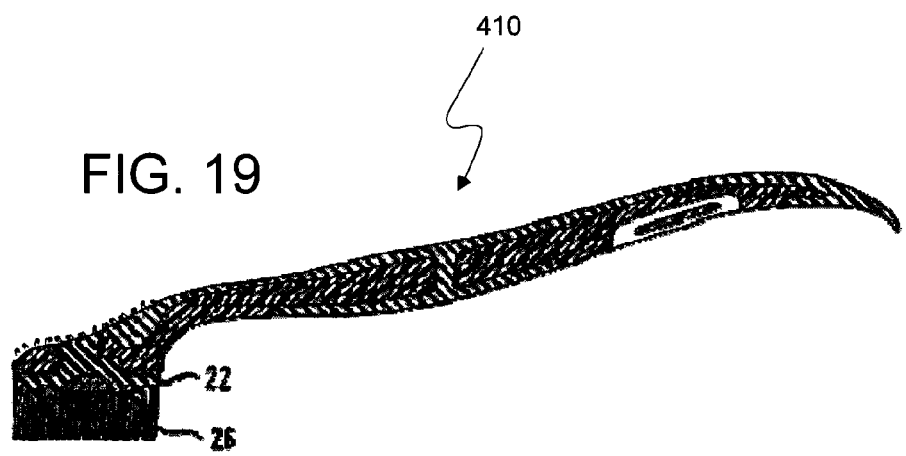
FIG. 19 is a cross-sectional side view of a toothbrush having the head shown in FIG. 11.

In one construction, the retaining members 81 are columnar-like structures that extend upwardly from the carrier 80. The retaining members 81 can curve inwardly to further assist in holding the bead or capsule in place. FIG. 19 illustrates a close-up cross-sectional view, showing such curved retaining members 81. Such curved retaining members 81 can have a length that extends more than halfway up (or down, depending on angle of view) the diameter of the bead or capsule 32 for retention. Hence, a length portion of the retaining members can be acutely disposed with respect to a vertical axis of the carrier 80 for retention. The combination of retaining members 81 provides a compressive force to hold the dispenser 32 in place. The inwardly disposed engaging surface 85 is generally smooth to reliably resist prematurely rupturing the dispenser 32 before use. (See FIG. 8) Also, the smooth and curved characteristic of engaging surface 85 provides for a generally uniform distribution of pressure on the surface of the dispenser 32. This construction thus reduces thin wall stress on the surface of the dispenser 32 to reliably resist prematurely rupturing the dispenser 32 before use. For example, shock forces acting on the toothbrush can be dissipated during transport operations.

The retaining members 81 can assist in rupturing the bead or capsule during brushing, and can have a flat surface at a distal end 82 to form a corner edge 83 against the bead or capsule for this purpose. With reference to FIGS. 8 and 10, some of the bristles 26 can extend from the retaining members 81. In this construction, a portion of the base of the bristle extends from a rear/back of the retaining member 81. This provides a compact space-saving head structure and also provides flow control benefits of the oral care material in the bristle field.

As illustrated in FIG. 10, the block 22 can be made of the same material as some or all of the bristles 26, as discussed above, which can be a different material from other portions of the handle. Alternatively, the handle and block can be made of the same material, with the bristles 26 being made of a different material.

Figure 11:
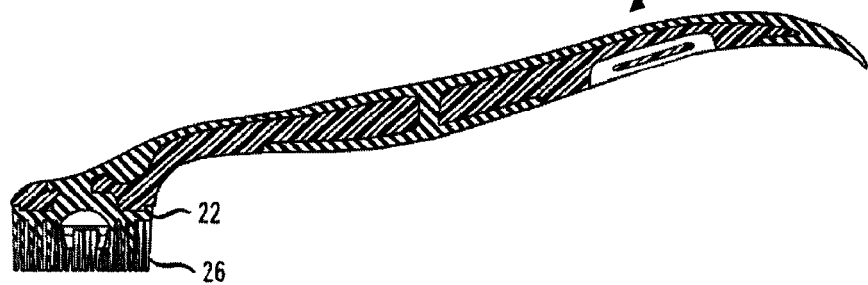
FIG. 11 is a cross-sectional side view of a toothbrush having the head shown in FIG. 10.

FIG. 11 illustrates a cross-sectional view of a toothbrush having the head or carrier structure shown in FIGS. 8-10. The carrier 80 can be angled at a 10.degree. angle with respect to the handle, representing a less-angled head than that shown in previous figures. An angle ranging from 80 to 12.degree. can assist in improving a user's brushing technique. As with FIG. 10, FIG. 11 also shows an example arrangement of materials, where the block 22 can be made of the same materials as some or all of the bristles 26 and portions of the handle. Alternatively, the handle can be made of the same material as the block 22 and/or bristles 26.

Hence, in some configurations, an oral care implement can include a rupturable dispenser with a dentifrice, as a connected unit or the various other combinations of components and materials as described. A toothbrush can have a toothpick which enables cleaning between the teeth. A dispenser containing a dentifrice or other oral care material can be connected in the bristle or cleaning element portion of the toothbrush for dispensing the dentifrice to the teeth to provide teeth cleaning and breath freshening or other oral care benefits to a user. In one construction, the oral care elements are configured to slow a radial flow of the oral care material released from the dispenser near an interior region of the carrier and increase a radial flow of the oral care material away from the interior region.

Figure 12:
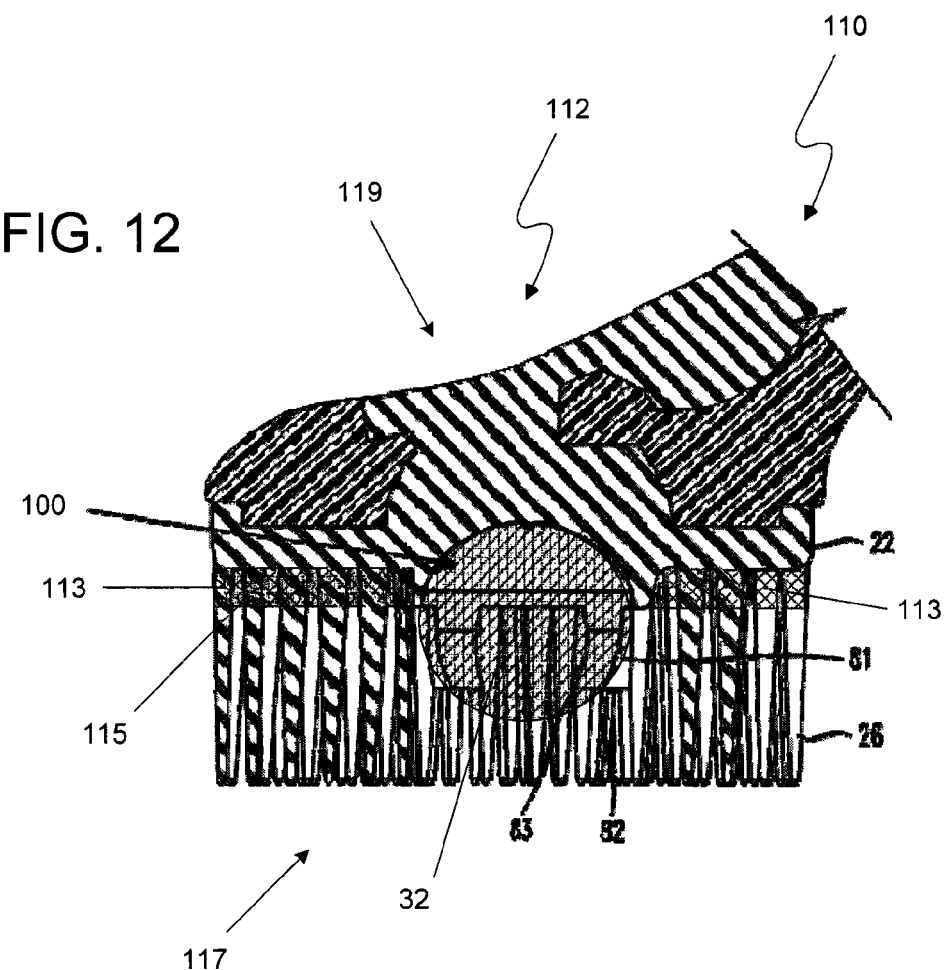
FIG. 12 is an enlarged cross-sectional side view of another configuration of the head of FIG. 9.
Figure 13:
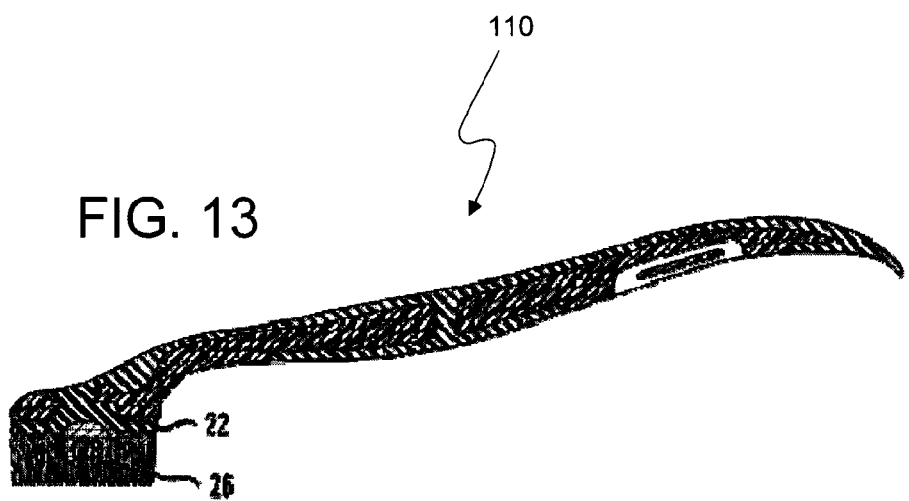
FIG. 13 is a cross-sectional side view of a toothbrush having the head shown in FIG. 11.

FIGS. 12-13 illustrate another configuration of an oral care implement in the form of a toothbrush 110 having a head 112 with a first face 117 and an opposite second face 119, which is generally the same as the toothbrush configuration of FIGS. 8-11, except as pertaining to film matrix 113. Film matrix 113 can be a relatively thin film containing one or more agents that can be rapidly released during use of the toothbrush. For example, film matrix 113 can be a starch, polymeric, gelatinous or other type of film configured to retain at least one agent 115 in a stable folin and to rapidly release the at least one agent when it comes into contact with saliva and/or is mechanically agitated during use of the toothbrush. Preferably, agent 115 includes a flavor agent, such as a breath freshener or flavorant, that is readily detectable by the user to provide a pleasing burst of flavor upon initial use of the toothbrush.

In one configuration, film matrix 113 can be a film matrix as described in U.S. Pat. No. 6,669,929, either with or without the inclusion of film flakes in the film matrix as described therein. Film matrix 113 can be formed from a matrix of hydroxyalkyl methylcellulose starch and starch film forming agents in which is entrained at least one agent 115, such as a colorant (e.g., a dye or pigment), flavorant, sweetener, breath freshener and/or therapeutic agent, such as an antibacterial agent. The film matrix can further include water, additional film forming agents, plasticizing agents, surfactants and emulsifying agents.

Film matrix 113 can be rupturable and/or dissolvable during use in the oral cavity so that flavors, sweeteners, therapeutic agents etc. entrained therein can be maintained substantially separate from dentifrice ingredients during manufacture and storage, such as dentifrice retained in store of dentifrice 132 or dentifrice applied to the toothbrush by the user. Agent 115 within film matrix 113 can be released when the film matrix comes into contact with saliva and/or via the mechanical agitation created during tooth brushing effecting rupture of the film matrix and release of the agent.

The Film Matrix

Film matrix 113 can be prepared by dissolving an hydroxyalkyl cellulose, a starch ingredient, an agent 115, and other film forming ingredients in a compatible solvent to form a film fowling composition (not shown). For the configuration of toothbrush 110, the film forming composition is preferably cast onto face first face 117 of head 112 and intermingled with tooth cleaning elements 26. For other configurations, the film forming composition can be sprayed directly on a portion of the toothbrush, such as on the tooth cleaning elements 26 (see e.g., FIG. 14), or cast in a cavity or recess formed in the toothbrush head (see e.g., FIG. 20). For additional configurations, the film forming composition can be cast on a releasable carrier (not shown) and dried to form a sheet of film matrix material, which can be cut or otherwise processed to form film matrix flakes or glitter that can be applied to various portions of the toothbrush, such as the tooth cleaning elements and/or soft tissue cleaning elements (see e.g. FIGS. 16, 18 and 20).

The thickness of film matrix 113 can range in size from 0.5 micron to 2 mm, but is preferably 2 to 100 microns and more preferably 2 to 10 microns. Additional stability can be provided to the dried film by applying a protective barrier overcoat (not shown) such as a food grade shellac or ethyl cellulose.

Film Substrate/Film Forming Agents

A major film forming agent that can be used to prepare a substrate for film matrix 113 according to one example is an hydroxyalkyl cellulose, such as hydroxypropyl methyl cellulose, hydroxyethylpropyl cellulose, hydroxybutyl methyl cellulose, hydroxy propyl methyl cellulose and carboxymethyl cellulose. Preferably the cellulose polymer is a low viscosity hydropropylmethyl cellulose polymer (HPMC). When HPMC is used as the film forming agent it is preferred that the HPMC have a viscosity in the range of about 1 to about 40 millipascal seconds (mPa·S) as determined as a 2% by weight aqueous solution of the HPMC at 20.degree. C. using a Ubbelohde tube viscometer. Preferably the HPMC has a viscosity of about 3 to about 20 mPa·s at 20.degree. C.

HPMC is available commercially from the Dow Chemical Company under the trade designation Methocel E5 LV. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a ubbelohde tube viscometer it has a viscosity of 5.1 mPascals at 20 degrees C.

The hydroxyalkyl methyl cellulose is incorporated in the film matrix in amounts ranging from about 10 to about 60% by weight and preferably about 15 to about 40% by weight.

Cold water swellable, physically modified and pregelatenized starches can be useful as texture modifiers to increase the stiffness of the hydroxyalkyl methyl cellulose film matrix. In the preparation of such starch products, the granular starch can be cooked in the presence of water and possibly an organic solvent at a temperature not higher than 10 degree C. higher than the gelatinization temperature. The obtained starch can then be dried.

Pregelatinized corn starch is available commercially, such as starch that is available under the trade designation Cerestar Polar Tex-Instant 12640 from the Cerestar Company. This Cerestar starch is a pregelaterized, stabilized and crosslinked waxy maize starch. It is readily dispersible and swellable in cold water. In its dry form, it is a white free flowing powder with an average flake size less than 180 micrometers and 85% of the flakes are smaller than 75 micrometers. It has a bulk density of 44 lbs/ft.sup.3.

The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor.

The pregelatinized starch can be present in film matrix 113 in an amount ranging from about 5 to about 50% by weight and preferably about 10 to about 35% by weight. The hydroxyalkyl cellulose to starch ratio (by weight) may vary from about 1:3 to about 4:1 and preferably about 1:1.5 to about 2.5:1.

Flavor Agents

Flavor agents can be incorporated in film matrix 113 including natural and artificial flavors to act as flavorings, breath fresheners, and/or sweeteners. These agents can include synthetic flavor oils and/or flavoring aromatics, oleo resins and extracts derived from plants, leaves, flowers, fruits and so forth, and combinations thereof Representative flavor oils can include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, can be used. Generally the flavoring agent is incorporated in film matrix 113 in an amount ranging from about 1 to about 30% by weight and preferably about 15 to about 25% by weight.

Sweeteners may also be incorporated in the film matrix and can include both natural and artificial sweeteners. Suitable sweeteners can include water soluble sweetening agents, such as monosaccharides, disaccharides and polysaccharides (e.g., xylose, ribose, glucose (dextrose), mannose, glatose, fructose (levulose), sucrose (sugar), maltose); and water soluble artificial sweeteners such as soluble saccharin salts (e.g., sodium or calcium saccharin salts), cyclamate salts, and dipeptide based sweeteners, such as L-aspartic acid derived sweeteners and L-aspartyl-L-phenylalaine methyl ester (aspartame).

In general, the effective amount of sweetener that provides the level of sweetness desired for a particular film matrix composition will vary with the sweetener selected. This amount can be about 0.01% to about 2% by weight of the composition.

Therapeutic Agents

Therapeutic agents can be incorporated in film matrix 113 and can include compounds that are reactive with dentifrice ingredients and should therefore be isolated from the dentifrice ingredients during manufacture and storage.

The therapeutic agents entrained in film matrix 113 can be maintained substantially separate from the ingredients of a dentifrice retained in store of dentifrice 32 during manufacture and storage of the toothbrush, which can be subsequently released into the dentifrice during tooth brushing. Entrainment of the therapeutic agent in film matrix 113 prevents leakage into the dentifrice so that in the case of therapeutic agents, which can be reactive ingredients, interaction with dentifrice ingredients is avoided.

For example, reaction of a cationic therapeutic agent such as cetyl pyridinium chloride or chlorhexidene with an anionic surfactant such as sodium lauryl sulfate, which surfactant is conventionally included in dentifrice compositions, inactivates the therapeutic agent thereby reducing the antibacterial efficacy of the dentifrice composition.

In the use of fluoride salts as anticavities agents, one of the methods used to achieve enhanced fluoridation known to the art (U.S. Pat. Nos. 5,045,305 and 5,145,668), is to mix, immediately before use, separate solutions containing fluoride and calcium salts. Such a procedure is a time consuming daily chore which discourages its use. Combining the calcium and fluoride salts into a single dentifrice composition will not provide an effective means for fluoridation as the presence of the calcium salt reacts with and removes bioactive soluble ionic fluoride from the dentifrice by forming insoluble and inactive calcium fluoride thereby reducing the antiocariogenic effectiveness of the fluoride dentifrice. Incorporating the calcium salt in the film matrix can isolate the fluoride ion in the dentifrice from interaction with the calcium salt until the film matrix disintegrates during tooth brushing.

Typically, in the case of calcium salts, these salts are present in the film matrix in an amount up to about 30% by weight, based on the weight of the film matrix, and preferably in the amount of about 18% to 22%.

In addition to fluoride or calcium salts, there can also be included in the film matrix anticalculus agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates, such as sodium hexametaphosphate, and cyclic phosphates, such as sodium trimetaphosphate, which can be included in the film matrix at a concentration of about 15 to 20% by weight.

Other active agents that can be incorporated in film matrix 113 include antibacterial agents such as Triclosan, breath freshening agents such as zinc gluconate, zinc citrate and/or alpha ionone, desensitizers such as potassium nitrate, vitamins such as pantheon, retinyl palmitate, tocopherol acetate, herbs such as chamomilla recutita, mentha piperita, salvia officinalis, commiphora myrrha, whitening agents such as hydrogen peroxide and urea peroxide, high cleaning silica, preservatives, silicones, and chlorophyll compounds.

The active agents can be included in the film matrix of the present invention at a concentration of about 0.1 to about 2.0% by weight and preferably about 0.15 to about 5% by weight.

Colorants

Colorants can be used to provide a desirable color for the film matrix that are pharmacologically and physiologically non-toxic when used in the suggested amounts. The colorants can include both pigments and dyes. Pigments can include non-toxic, water insoluble inorganic pigments such as titanium dioxide, titanium dioxide coated mica (Timiron), chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments can have a flake size in the range of 5 to 1000 microns, preferably 250 to 500 microns. Pigments can be incorporated in film matrix 113 in an amount ranging from about 1 to about 10% by weight and preferably about 2 to about 5% by weight.

A particularly preferred class of dyes are those available from Micropowders, Inc. under the trade designation Spectra bead which are high molecular weight polyethylene powders permanently colored with dyes such as FD&C Blue #1 aluminum lake.

Dyes used for the film matrix can be distributed uniformly throughout the film matrix and are desirably food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfoni-c acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfonium-phenyl)-methylene}-[1-(N-ethyl-N-p-sulfobenzyl)-.DELTA.-3,5-cyclohexadienimine], FD&C Blue No. 1 (disodium salt of dibenzyldiethyl-diaminotriphenylcarbinol trisulfonic acid anhydrite), FD&C Blue No. 2

(sodium salt of disulfonic acid of indigotin) and mixtures thereof in various proportions. The concentration of the dye present in the film matrix can be in an amount ranging from about 0.5 to about 5 and preferably about 1 to about 4% by weight.

Figure 14:
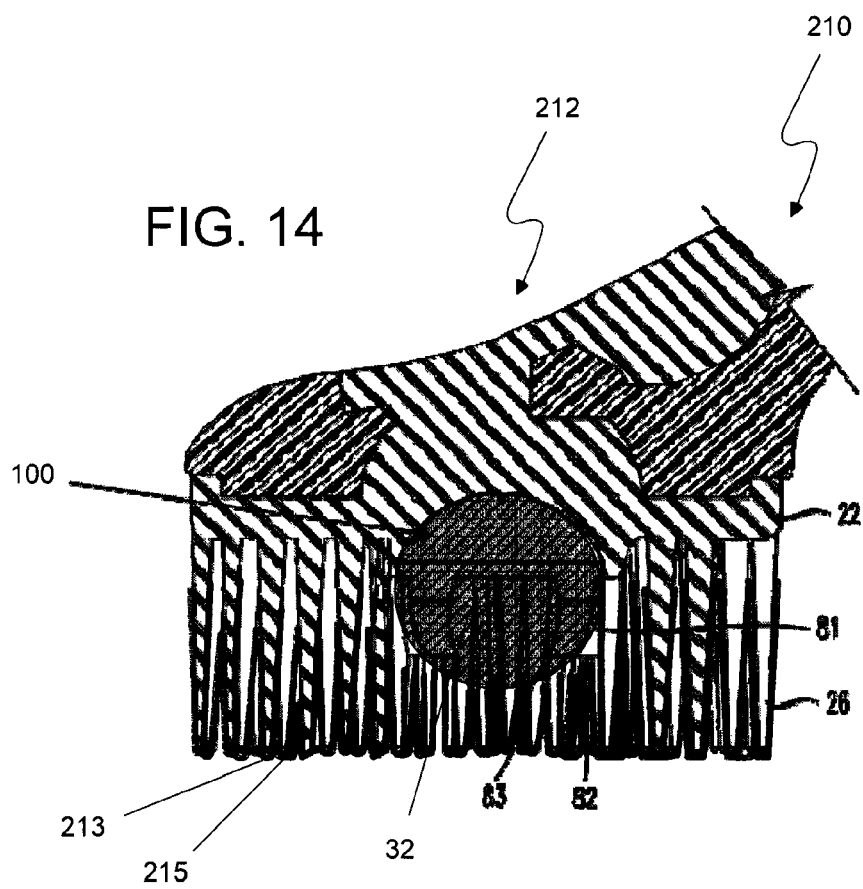
FIG. 14 is an enlarged cross-sectional side view of yet another configuration of the head of FIG. 9.
Figure 15:
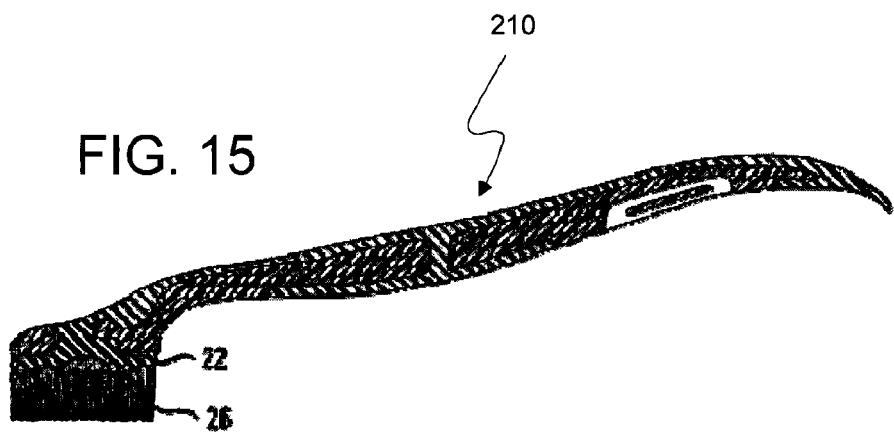
FIG. 15 is a cross-sectional side view of a toothbrush having the head shown in FIG. 11.

FIGS. 14-15 illustrate another configuration of an oral care implement in the form of a toothbrush 210 having a head 212, which is similar to the toothbrush configuration of FIGS. 12-13, except as pertaining to film coating 213. Film coating 213 is a form of a film matrix, like film matrix 113, except that it is in the form of a coating covering at least a portion of tooth cleaning elements 26. As described above for film matrix 113, film coating 213 can be formed via spraying the film forming composition directly on a portion of the toothbrush, such as on the tooth cleaning elements 26. Toothbrush 213 provides a configuration in which the film matrix quickly makes contact with teeth, oral tissues and/or saliva during initial use of the toothbrush and experiences significant mechanical agitation, which enhances the speed at which the one or more rapidly releasable agents 215 retained therein can be released. Thus, toothbrush 213 can provide a very quick and intense burst of flavor to the user upon initial use of the toothbrush.

Figure 16:
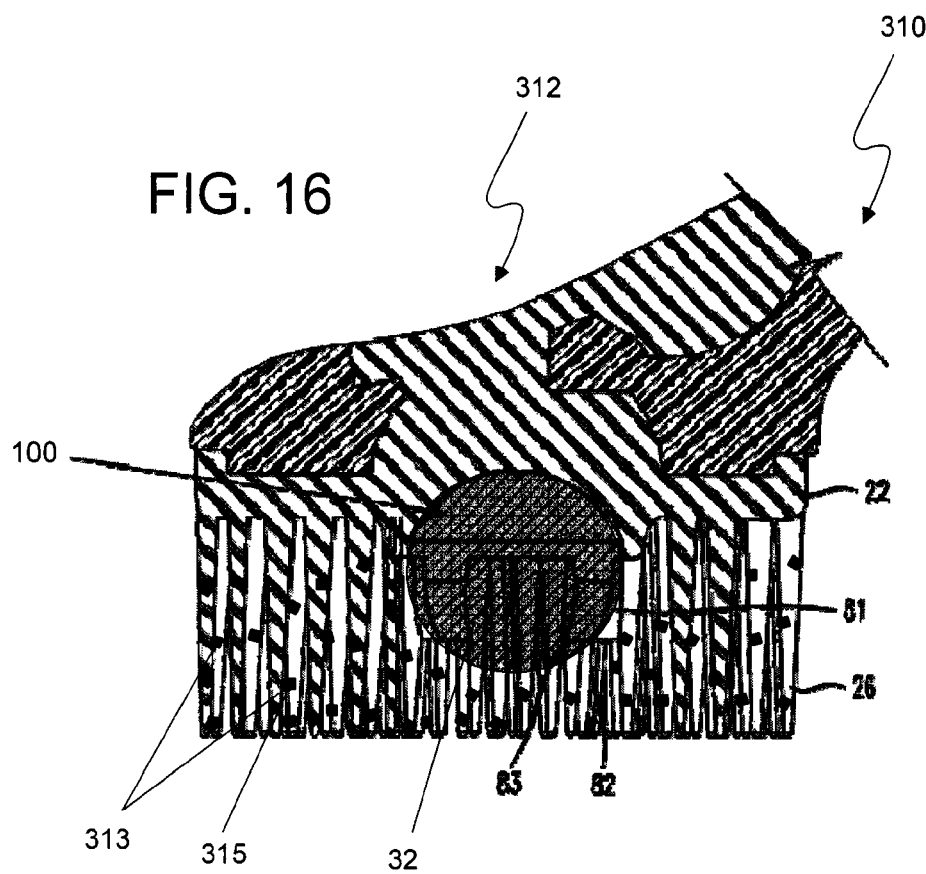
FIG. 16 is an enlarged cross-sectional side view of a further configuration of the head of FIG. 9.

FIGS. 16-17 illustrate another configuration of an oral care implement in the form of a toothbrush 310 having a head 312 that is similar to the toothbrush configuration of FIGS. 12-13, except as pertaining to film glitter or film flakes 313. Film flakes 313 are a particle or flake form of a film matrix, like film matrix 113, except that it is in the form of pieces or particles of a film matrix that are attached to portions of tooth cleaning elements 26 or other portions of the toothbrush.

As described above for film matrix 113, film flakes 313 can be formed via casting a film forming composition on a releasable carrier or mold (not shown) and dried to form a sheet of film matrix material. The carrier material preferably has a surface tension that allows the film solution to spread evenly across the intended carrier width without soaking to form a destructive bond with the film carrier substrates. Examples of suitable carrier materials can include glass, stainless steel, Teflon and polyethylene-impregnated paper. Drying of the film may be carried out at high temperature using a drying oven, drying terminal, vacuum drier, or any other suitable drying equipment that does not adversely affect the ingredients of which the film is composed.

The dried film matrix can subsequently be cut, punched, shredded or otherwise processed into shaped particles, flakes or glitter having a particle size of 0.005 to 0.125 inches and preferably 0.01 to 0.05 inches. Additional stability can be provided to the formed shapes by applying to the film, before shaping into flakes, a protective barrier overcoat such as a food grade shellac or ethyl cellulose. When the film flakes are to be used for decorative effect, the dried film matrix can be formed into various attractively shaped flakes such as hearts, stars, diamonds and circles. Film matrix flakes 313 can include colorants to provide an aesthetically pleasing appearance, such as a glitter appearance.

Film flakes 313 can be applied to various portions of the toothbrush, such as the tooth cleaning elements and/or soft tissue cleaning elements. Film flakes 313 can be applied to tooth cleaning elements 26 while they are wet via spraying or dusting the flakes onto the tooth cleaning elements. The film matrix flakes can also be applied via dipping the wet tooth cleaning elements into a stock of film flakes. The film matrix flakes can adhere to the tooth cleaning elements via partial dissolution of the film matrix in the water droplets thereon and remain attached to the tooth cleaning elements when dried. Alternatively, the film matrix flakes can be attached via a food grade adhesive.

Figure 18:
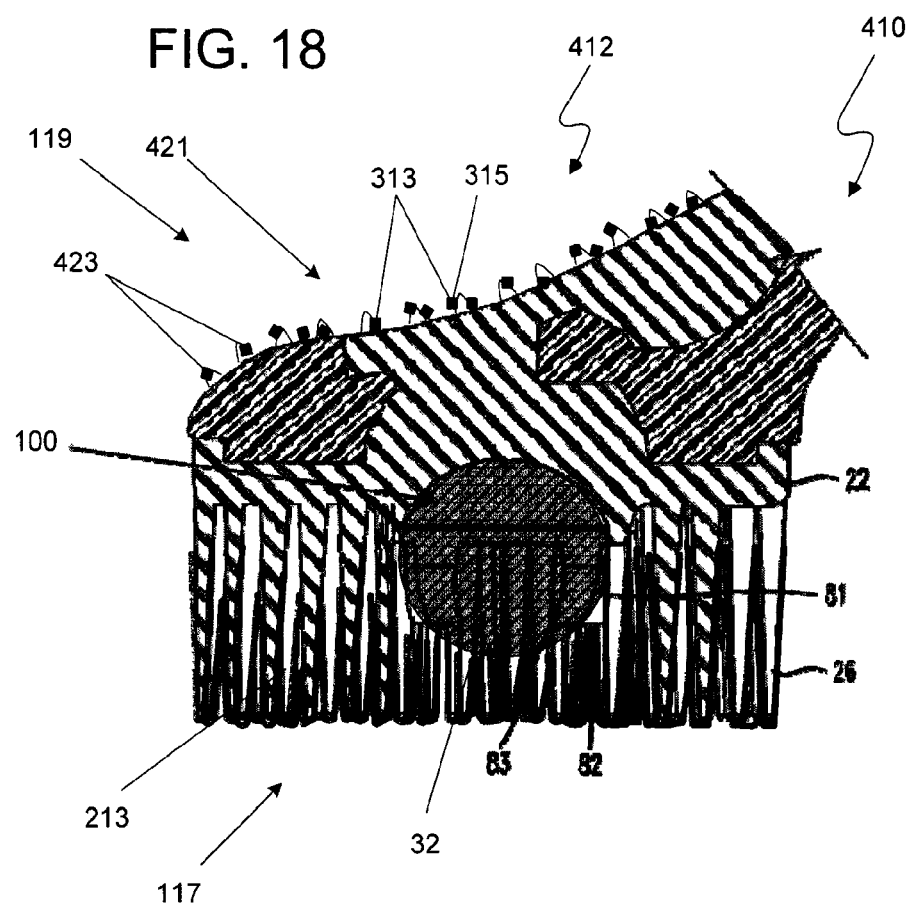
FIG. 18 is an enlarged cross-sectional side view of an additional configuration of the head of FIG. 9.

FIGS. 18-19 illustrate another configuration of an oral care implement in the form of a toothbrush 410 having a head 412, which is similar to the toothbrush configuration of FIGS. 14-17, except as pertaining to the soft tissue cleaner 421 and the location of film glitter or film flakes 313. As shown, toothbrush 410 includes film coating 213 disposed on tooth brush cleaning elements 26 similar to toothbrush 210, as well as film flakes 313 disposed on soft tissue cleaning elements 423 of soft tissue cleaner 421, rather than being disposed on the tooth cleaning elements as in toothbrush 310. Soft tissue cleaner 421 can be disposed on second face 119 of toothbrush head 412, which is preferably opposite first face 117 from which tooth cleaning elements 26 extend.

The soft tissue cleaner 421 includes soft tissue cleaning elements 423, which are configured to clean soft tissues in the mouth, such as the tongue and interior surfaces of the cheeks, lips or gums, by facilitating the removal of microflora and other debris and by distributing dentifrice—especially in the recesses of adjacent papillae of the tongue. Further, soft tissue elements 423 can improve the dissolution and dispersion of dentifrice in the oral cavity during use, as well as the dissolution and dispersion of agents 315 released from film flakes 313 or film coating 213. Soft tissue cleaning elements 423 are shown in FIGS. 18 and 19 as protrusions, which can include nubs. However, it is understood that various types and configurations of soft tissue cleaning elements can be used, such as ridges, nubs, scrapers, bumps, sponges, fabrics, etc. in various combinations. As shown, soft tissue elements 423 can include protrusions made from TPE materials, which are rubbery and soft. In addition, soft tissue elements 423 can include protrusions made from LLDPE materials, which are still soft, but have superior flow characteristics that are well suited to filling very thin sections, and thus, can be more easily manufactured and can be manufactured to have thinner profiles.

Figure 20:
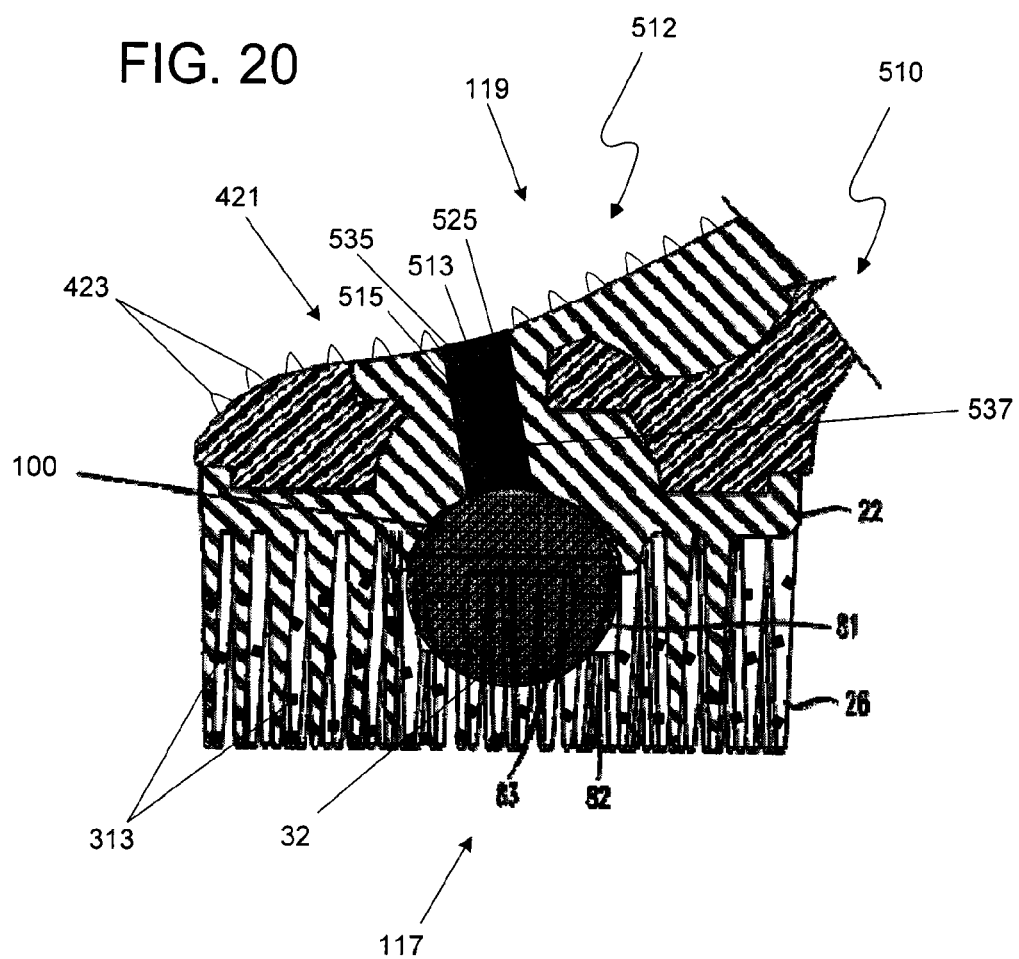
FIG. 20 is an enlarged cross-sectional side view of another configuration of the head of FIG. 9.
Figure 21:
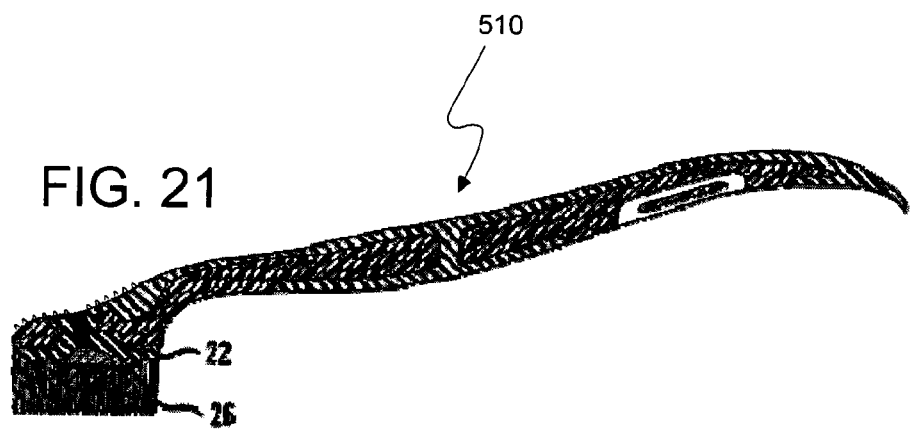
FIG. 21 is a cross-sectional side view of a toothbrush having the head shown in FIG. 11.

FIGS. 20-21 illustrate another configuration of an oral care implement in the form of a toothbrush 510 having a head 512, which is similar to the toothbrush configuration of FIGS. 16-19, except as pertaining to film matrix 513 and recess 525. Recess 525 is a cavity formed in head 512 at second face 119 within which film matrix 513 can be retained. Similar to film matrix 113, film matrix 513 can be formed by pouring or casting the film forming composition into recess 525. During use, an upper portion 535 of film matrix 513 can provide a rapid burst of flavor to the user when it comes into contact with saliva and/or oral tissues, such as the surface of the tongue or the inside of the cheeks followed by a more prolonged release of agents 515 disposed in lower portions 537 of film matrix 513.

Depending upon the configuration of film matrix 513, such as its release rate for the agents retained therein, its dissolvability or the type of agent or agents retained therein, recess 525 can have a variety of configurations. For instance, it could be a relatively wide and shallow cavity (not shown) that can provide a large surface area at upper portion 535 without providing a prolonged release rate. Further, recess 525 can include a plurality of cavities disposed on first face 117, second face 119, and/or other locations on the toothbrush head. In the configuration shown in FIG. 20, recess 525 is in the form of a channel extending between second face 119 and a store of dentifrice 32. Thus, upon depletion of film matrix 513, dentifrice can be released from the store of dentifrice 32 to second face 119 and soft tissue cleaner 421. The dentifrice can be dispensed quickly when dispensed simultaneously to the plurality of faces, can be distributed quickly and effectively by the plurality of cleaners (e.g., tooth and tongue cleaners) on the multiple faces, and can be dispensed directly to the oral regions being cleaned.

Other configurations will be apparent to those skilled in the art from consideration of the specification disclosed herein. It is intended that the specification and examples be considered as exemplary only, with the true scope and spirit of the invention being indicated by the following claims.

What is claimed is:

1. An oral care implement comprising:
   a handle;
   a head having a first face and a second face, a recess formed into the head at the second face;
   tooth cleaning elements extending from the first face of the head and soft tissue cleaning elements extending from the second face of the head;
   a store of dentifrice retained at the head;
   a film strip disposed within the recess; and
   a first dentifrice path providing communication between the first face and the store of dentifrice, wherein upon depletion of the film strip from the recess, the recess forms a second dentifrice path providing communication between the second face and the store of dentifrice.

2. An oral care implement comprising:
   a handle;
   a head having a first face and a second face, a recess formed into the head at the second face;
   tooth cleaning elements extending from the first face of the head and soft tissue cleaning elements extending from the second face of the head;
   a store of dentifrice retained at the head;
   a film matrix containing at least one rapidly releasable agent, wherein the film matrix comprises a film strip disposed within the recess; and
   wherein the recess is a channel extending from the store of dentifrice to an opening in the second face of the head.

3. The oral care implement of claim 2 wherein upon depletion of the film strip from the recess, the channel forms a passageway from the store of dentifrice to the opening in the second face of the head so that dentifrice can be released from the store of dentifrice to the soft tissue cleaning elements on the second face of the head.

4. An oral care implement comprising:
   a handle;
   a head;
   an arrangement of tooth cleaning elements on a lint surface of the head;
   a first path providing a first flow of dentifrice from a store of dentifrice retained at the head to the tooth cleaning elements;
   an arrangement of soft tissue cleaning elements on a second surface of the head;
   a film matrix containing at least one rapidly releasable agent disposed within a recess formed into the second surface of the head, the at least one rapidly releasable agent flowing to the soft tissue cleaning elements during use of the oral care implement; and
   wherein upon depletion of the film matrix from the recess, the recess forms a second path providing a second flow of dentifrice from the store of dentifrice to the soft tissue cleaning elements.

5. The oral care implement of claim 4, wherein the film matrix is a first film matrix, the oral care implement further comprising a second film matrix configured to provide at least one rapidly releasable agent to the tooth cleaning elements.

6. The oral care implement of claim 4, wherein the second flow is greater than the first flow.

7. The oral care implement of claim 4, wherein the first flow is substantially the same as the second flow.

8. The oral care implement of claim 4, wherein the first store of dentifrice includes a first dentifrice and the at least one rapidly releasable agent includes a second dentifrice.

* * * * *